(12) United States Patent
Taki

(10) Patent No.: US 12,097,062 B2
(45) Date of Patent: Sep. 24, 2024

(54) ESTIMATION DEVICE, ESTIMATION METHOD, AND ESTIMATION PROGRAM

(71) Applicant: FUJIFILM Corporation, Tokyo (JP)

(72) Inventor: Tomoko Taki, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 17/841,347

(22) Filed: Jun. 15, 2022

(65) Prior Publication Data

US 2023/0017704 A1 Jan. 19, 2023

(30) Foreign Application Priority Data

Jul. 14, 2021 (JP) .................. 2021-116426

(51) Int. Cl.
- *A61B 6/00* (2024.01)
- *A61B 6/03* (2006.01)
- *A61B 6/50* (2024.01)

(52) U.S. Cl.
CPC .............. *A61B 6/482* (2013.01); *A61B 6/032* (2013.01); *A61B 6/505* (2013.01)

(58) Field of Classification Search
CPC ......... A61B 6/482; A61B 6/032; A61B 6/505; A61B 6/5217
See application file for complete search history.

(56) References Cited

U.S. PATENT DOCUMENTS

| | | |
|---|---|---|
| 5,432,834 A | 7/1995 | Gershman |
| 5,657,369 A | 8/1997 | Stein et al. |
| 5,687,211 A | 11/1997 | Berger et al. |
| 5,717,735 A | 2/1998 | Ramsdell et al. |
| 5,748,705 A | 5/1998 | Stein et al. |
| 5,771,272 A | 6/1998 | Berger et al. |
| 5,778,045 A | 7/1998 | von Stetten et al. |
| 5,835,555 A | 11/1998 | Barry et al. |
| 5,835,562 A | 11/1998 | Ramsdell et al. |
| 5,838,765 A | 11/1998 | Gershman et al. |
| 6,009,147 A | 12/1999 | Stein et al. |

(Continued)

FOREIGN PATENT DOCUMENTS

| | | |
|---|---|---|
| JP | H09-108206 A | 4/1997 |
| JP | 2006-271437 A | 10/2006 |

(Continued)

*Primary Examiner* — David P Porta
*Assistant Examiner* — Meenakshi S Sahu
(74) *Attorney, Agent, or Firm* — Studebaker & Brackett PC

(57) ABSTRACT

A processor functions as a trained neural network that derives an estimation result relating to a three-dimensional bone density of a bone part from a simple radiation image acquired by simply imaging a subject including the bone part, or a DXA scanning image acquired by imaging the subject by a DXA method. The trained neural network learns using, as teacher data, (i) two radiation images or the like acquired by imaging the subject including the bone part with radiation having different energy distributions, and a two-dimensional bone density of the bone part included in the two radiation images or the like, or (ii) the radiation image or the like of the subject or a bone part image representing the bone part of the subject, the two-dimensional bone density of the bone part included in the radiation image or the like, or the bone part image, and the three-dimensional bone density of the bone part of the subject.

10 Claims, 13 Drawing Sheets

(56) References Cited

U.S. PATENT DOCUMENTS

| | | |
|---|---|---|
| 6,059,455 A | 5/2000 | Cabral |
| 6,217,214 B1 | 4/2001 | Cabral et al. |
| 2011/0305405 A1 | 12/2011 | Kawamura |
| 2016/0140720 A1 | 5/2016 | Naito |
| 2018/0122094 A1 | 5/2018 | Naito |
| 2022/0051398 A1* | 2/2022 | Watanabe ................ G06T 7/11 |
| 2022/0335605 A1* | 10/2022 | Taki ...................... A61B 6/032 |

FOREIGN PATENT DOCUMENTS

| | | |
|---|---|---|
| JP | 2011-255060 A | 12/2011 |
| JP | 2015-043959 A | 3/2015 |
| JP | 2020-171785 A | 10/2020 |

* cited by examiner

ESTIMATION DEVICE, ESTIMATION METHOD, AND ESTIMATION PROGRAM

CROSS REFERENCE TO RELATED APPLICATIONS

The present application claims priority under 35 U.S.C. § 119 to Japanese Patent Application No. 2021-116426 filed on Jul. 14, 2021. The above application is hereby expressly incorporated by reference, in its entirety, into the present application.

BACKGROUND

Technical Field

The present disclosure relates to an estimation device, an estimation method, and an estimation program.

Related Art

A dual X-ray absorptiometry (DXA) method is known as one of the typical bone mineral quantification methods that are used to diagnose a bone density in a bone-related disease, such as osteoporosis. The DXA method is a method of calculating a bone mineral density from a pixel value of a radiation image obtained by performing imaging by the radiation of two types of energies by using radiation incident on and transmitted through a human body, which is attenuated by an attenuation coefficient $\mu$ ($cm^2/g$), a density $\rho$ ($g/cm^3$) and a thickness t (cm), which depend on a substance (for example, a bone) that configures the human body.

In addition, various methods for evaluating the bone density using a radiation image acquired by imaging a subject have been proposed. For example, JP2020-171785A proposes a method of estimating information relating to the bone density, such as a bone mineral density per unit volume, from an image in which the bone appears by using a trained neural network constructed by training a neural network. In the method disclosed in JP2020-171785A, the neural network learns using the image in which the bone appears acquired by simple imaging and the bone density acquired by the DXA method as teacher data.

Here, simple imaging is an imaging method of acquiring one two-dimensional image, which is a transmission image of the subject, by emitting the radiation to the subject once. In the following description, the radiation image acquired by simple imaging will be referred to as a simple radiation image.

However, it is desired to estimate the bone density with higher accuracy.

SUMMARY OF THE INVENTION

The present disclosure has been made in view of the above circumstances, and is to enable estimation of a three-dimensional bone density with high accuracy.

The present disclosure relates to an estimation device comprising at least one processor, in which the processor functions as a trained neural network that derives an estimation result relating to a three-dimensional bone density of a bone part from a simple radiation image acquired by simply imaging a subject including the bone part, or a DXA scanning image acquired by imaging the subject by a DXA method, and the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image, of the subject or a bone part image representing the bone part of the subject, the two-dimensional bone density of the bone part included in the radiation image, the DXA scanning image, or the bone part image, and the three-dimensional bone density of the bone part of the subject.

Note that, in the estimation device according to the present disclosure, the three-dimensional bone density may be derived from a three-dimensional image of the subject.

In addition, in the estimation device according to the present disclosure, the three-dimensional image may be a CT image.

In addition, in the estimation device according to the present disclosure, the three-dimensional bone density may be obtained by specifying a bone region in the CT image, deriving an attenuation coefficient of radiation in the bone region, and deriving the three-dimensional bone density based on a bone density at each position in the bone region, which is derived based on the attenuation coefficient of the radiation and a mass attenuation coefficient in the bone region.

In addition, in the estimation device according to the present disclosure, the two-dimensional bone density may be derived from the two radiation images or the DXA scanning image.

In addition, in the estimation device according to the present disclosure, the two-dimensional bone density may be derived based on a body thickness distribution of the subject estimated based on at least one radiation image of the two radiation images or the DXA scanning image, an imaging condition in a case of acquiring the two radiation images or the DXA scanning image, and a pixel value of a bone region in the bone part image obtained by extracting the bone part, which is derived by energy subtraction processing of performing weighting subtraction on the two radiation images or the DXA scanning image.

In addition, in the estimation device according to the present disclosure, the two-dimensional bone density may be derived from the bone part image.

In addition, in the estimation device according to the present disclosure, the two-dimensional bone density may be derived based on a body thickness distribution of the subject estimated based on the radiation image or the DXA scanning image, an imaging condition in a case of acquiring the radiation image or the DXA scanning image, and a pixel value of a bone region in the bone part image.

The present disclosure relates to an estimation method comprising using a trained neural network that derives an estimation result relating to a three-dimensional bone density of a bone part from a simple radiation image acquired by simply imaging a subject including the bone part, or a DXA scanning image acquired by imaging the subject by a DXA method to derive the estimation result relating to the three-dimensional bone density of the bone part, in which the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image of the subject or a bone part image representing the bone part of the subject, the two-dimensional bone density of the bone part included in the radiation image, the DXA scanning image, or the bone part image, and the three-dimensional bone density of the bone part of the subject.

The present disclosure relates to an estimation program causing a computer to execute a procedure comprising using a trained neural network that derives an estimation result relating to a three-dimensional bone density of a bone part from a simple radiation image acquired by simply imaging a subject including the bone part, or a DXA scanning image acquired by imaging the subject by a DXA method to derive the estimation result relating to the three-dimensional bone density of the bone part, in which the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image of the subject or a bone part image representing the bone part of the subject, the two-dimensional bone density of the bone part included in the radiation image, the DXA scanning image, or the bone part image, and the three-dimensional bone density of the bone part of the subject.

According to the present disclosure, it is possible to estimate the three-dimensional bone density with high accuracy.

DETAILED DESCRIPTION

Figure 1:
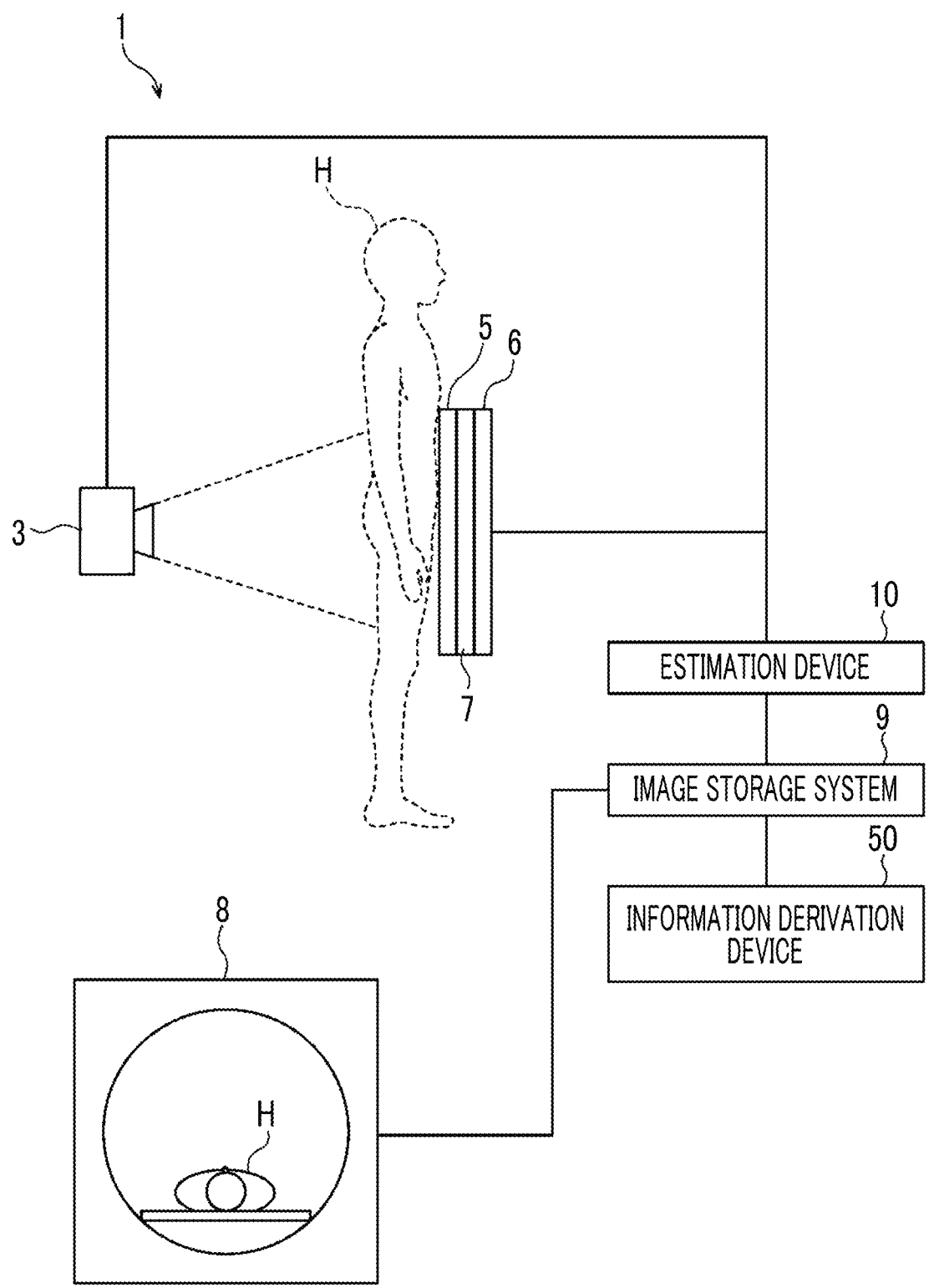
FIG. 1 is a schematic block diagram showing a configuration of a radiography system to which an estimation device according to an embodiment of the present disclosure is applied.

In the following, an embodiment of the present disclosure will be described with reference to the drawings. FIG. 1 is a schematic block diagram showing a configuration of a radiography system to which an estimation device according to an embodiment of the present disclosure is applied. As shown in FIG. 1, the radiography system according to the present embodiment comprises an imaging apparatus 1, a CT device 8, an image storage system 9, an estimation device 10 according to the present embodiment, and an information derivation device 50. The imaging apparatus 1, the computed tomography (CT) device 8, the estimation device 10, and the information derivation device 50 are connected to the image storage system 9 via a network (not shown).

The imaging apparatus 1 is an imaging apparatus capable of performing energy subtraction using a so-called one-shot method of irradiating a first radiation detector 5 and a second radiation detector 6 with radiations such as X-rays which is emitted from a radiation source 3 and is transmitted through a subject H while changing energies. At the time of imaging, as illustrated in FIG. 1, the first radiation detector 5, a radiation energy conversion filter 7 that consists of, for example, a copper plate, and the second radiation detector 6 are disposed in this order from the side closer to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. Therefore, the first radiation image G1 and the second radiation image G2 are acquired by imaging the subject H with the radiation having different energy distributions. The first and second radiation images G1 and G2 are input to the estimation device 10. Both the first radiation image G1 and the second radiation image G2 are front images including a periphery of a crotch of the subject H.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

In addition, the imaging apparatus 1 can also acquire a simple radiation image G0 which is a simple two-dimensional image of the subject H by performing a simple imaging of the subject H by using only the first radiation detector 5. The imaging for acquiring the first and second radiation images G1 and G2 is referred to as energy subtraction imaging in order to distinguish the imaging from simple imaging. In the present embodiment, the first and second radiation images G1 and G2 acquired by energy subtraction imaging are used as learning data to be described below. In addition, the simple radiation image G0 acquired by simple imaging is used for deriving an estimation result relating to a bone density as described below.

The CT device 8 acquires a plurality of tomographic images representing a plurality of tomographic planes of the subject H as a three-dimensional CT image V0. The CT value of each pixel (voxel) in the CT image is a numerical value of the radiation absorbance in the composition constituting the human body. The CT value will be described below.

The image storage system 9 is a system that stores the image data of the radiation image acquired by the imaging apparatus 1 and the image data of the CT image acquired by the CT device 8. The image storage system 9 extracts an image corresponding to requests from the estimation device 10 and the information derivation device 50 from the stored radiation image and CT image and transmits the extracted image to a request source device. Specific examples of the image storage system 9 include picture archiving and communication systems (PACS). Note that, in the present embodiment, the image storage system 9 stores a large amount of teacher data for training the neural network described below.

Figure 2:
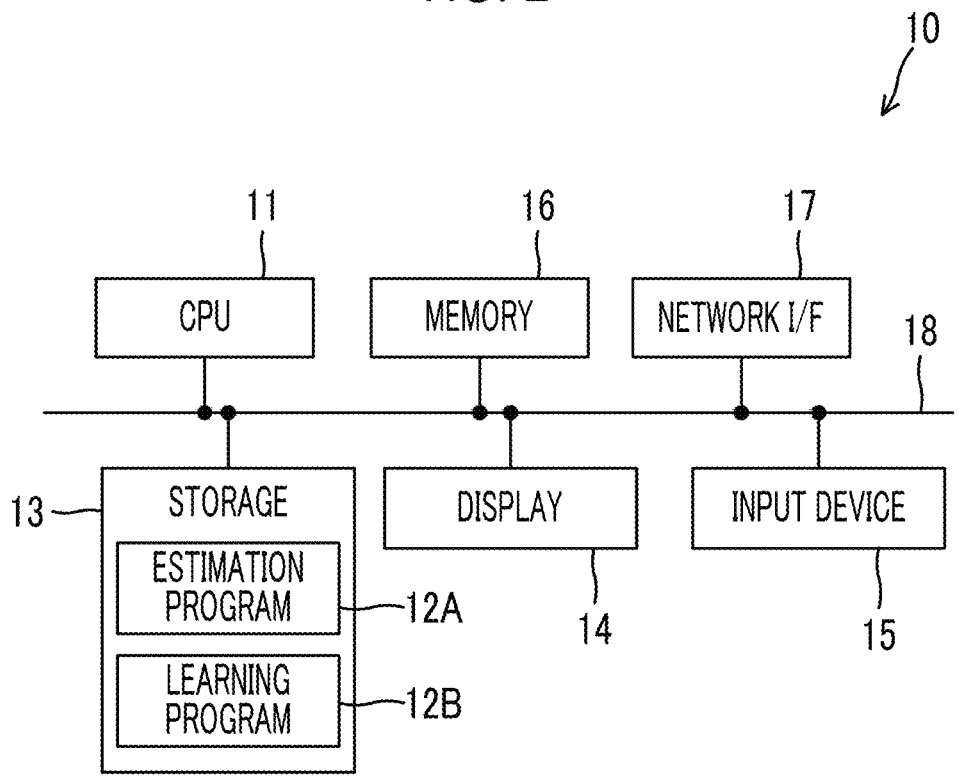
FIG. 2 is a diagram showing a schematic configuration of the estimation device according to the present embodiment.

Then, the estimation device according to the present embodiment will be described. First, a hardware configuration of the estimation device according to the present embodiment will be described with reference to FIG. 2. As shown in FIG. 2, the estimation device 10 is a computer, such as a workstation, a server computer, and a personal computer, and comprises a central processing unit (CPU) 11, a non-volatile storage 13, and a memory 16 as a transitory storage region. In addition, the estimation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. The CPU 11 is an example of a processor according to the present disclosure.

The storage 13 is realized by a hard disk drive (HDD), a solid state drive (SSD), a flash memory, and the like. The storage 13 as a storage medium stores an estimation program 12A and a learning program 12B installed in the estimation device 10. The CPU 11 reads out the estimation program 12A and the learning program 12B from the storage 13, expands the estimation program 12A and the learning program 12B in the memory 16, and executes the expanded estimation program 12A and the expanded learning program 12B.

Note that the estimation program 12A and the learning program 12B are stored in a storage device of the server computer connected to the network or in a network storage in a state of being accessible from the outside, and are downloaded and installed in the computer that configures the estimation device 10 in response to the request. Alternatively, the estimation program 12A and the learning program 12B are distributed in a state of being recorded on a recording medium, such as a digital versatile disc (DVD) or a compact disc read only memory (CD-ROM), and are installed in the computer that configures the estimation device 10 from the recording medium.

Figure 3:
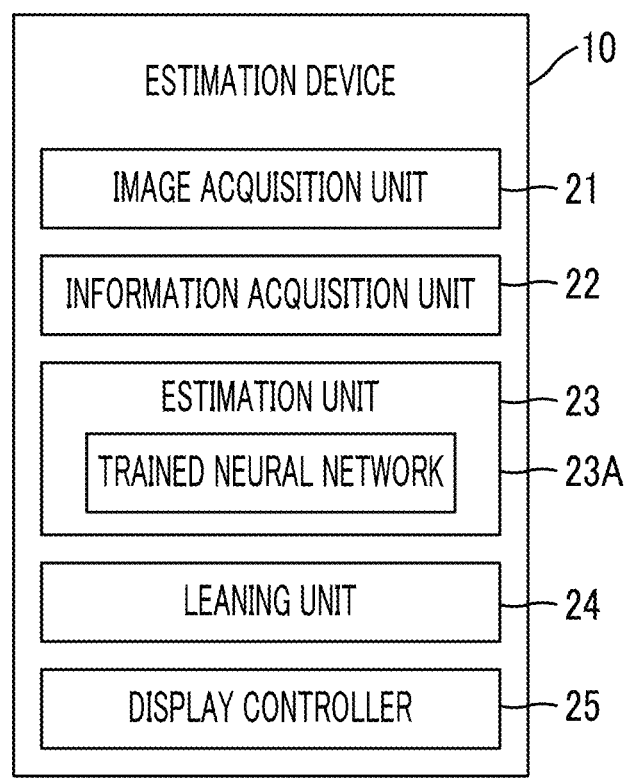
FIG. 3 is a diagram showing a functional configuration of the estimation device according to the present embodiment.

Then, a functional configuration of the estimation device according to the present embodiment will be described. FIG. 3 is a diagram showing the functional configuration of the estimation device according to the present embodiment. As shown in FIG. 3, the estimation device 10 comprises an image acquisition unit 21, an information acquisition unit 22, an estimation unit 23, a learning unit 24, and a display controller 25. Further, the CPU 11 functions as the image acquisition unit 21, the information acquisition unit 22, the estimation unit 23, and the display controller 25 by executing the estimation program 12A. In addition, the CPU 11 functions as the learning unit 24 by executing the learning program 12B.

The image acquisition unit 21 acquires, for example, the first radiation image G1 and the second radiation image G2 which are the front images of the vicinity of the crotch of the subject H from the first and second radiation detectors 5 and 6 by causing the imaging apparatus 1 to perform energy subtraction imaging of the subject H. In a case in which the first radiation image G1 and the second radiation image G2 are acquired, an imaging conditions, such as an imaging dose, a radiation quality, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by an operator. The set imaging condition is stored in the storage 13. The first and second radiation images G1 and G2 acquired by energy subtraction imaging, and the imaging conditions are also transmitted to and stored in the image storage system 9.

In addition, the image acquisition unit 21 acquires the simple radiation image G0 which is the front image of the vicinity of the crotch of the subject H by causing the imaging apparatus 1 to perform the simple imaging of the subject H by using only the first radiation detector 5.

Note that, in the present embodiment, the first and second radiation images G1 and G2, and the simple radiation image G0 may be acquired by a program separate from the estimation program 12A and stored in the storage 13. In this case, the image acquisition unit 21 acquires the first and second radiation images G1 and G2, and the simple radiation image G0 stored in the storage 13 by reading out the first and second radiation images G1 and G2, and the simple radiation image G0 from the storage 13 for processing.

The information acquisition unit 22 acquires the teacher data for training a neural network, which will be described below, from the image storage system 9 via the network I/F 17.

The estimation unit 23 derives the estimation result relating to the three-dimensional bone density of the bone part included in the subject H from the simple radiation image G0. In the present embodiment, the estimation result relating to the three-dimensional bone density of a target bone in a bone region included in the simple radiation image G0 is derived as the estimation result of the three-dimensional bone density. Therefore, the estimation unit 23 derives the estimation result relating to the three-dimensional bone density by using a trained neural network 23A that outputs the three-dimensional bone density in a case in which the simple radiation image G0 is input.

Here, for the estimation result relating to the three-dimensional bone density, the bone density per unit volume of each pixel included in the bone part of the subject H in the simple radiation image G0, or a representative value of the bone density per unit volume of each pixel included in a region of the target bone in the bone part can be used. In the present embodiment, the target bone is the femur, and the representative value of the bone density per unit volume of each pixel included in the femur is derived as the estimation result relating to the three-dimensional bone density.

The learning unit 24 constructs the trained neural network 23A by subjecting the neural network to machine learning using the teacher data. Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
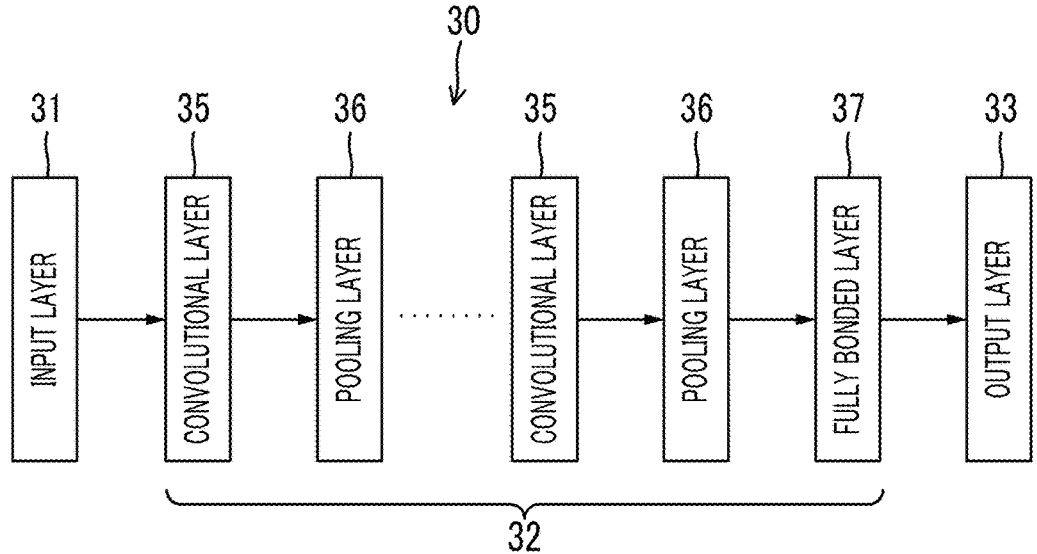
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Moreover, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
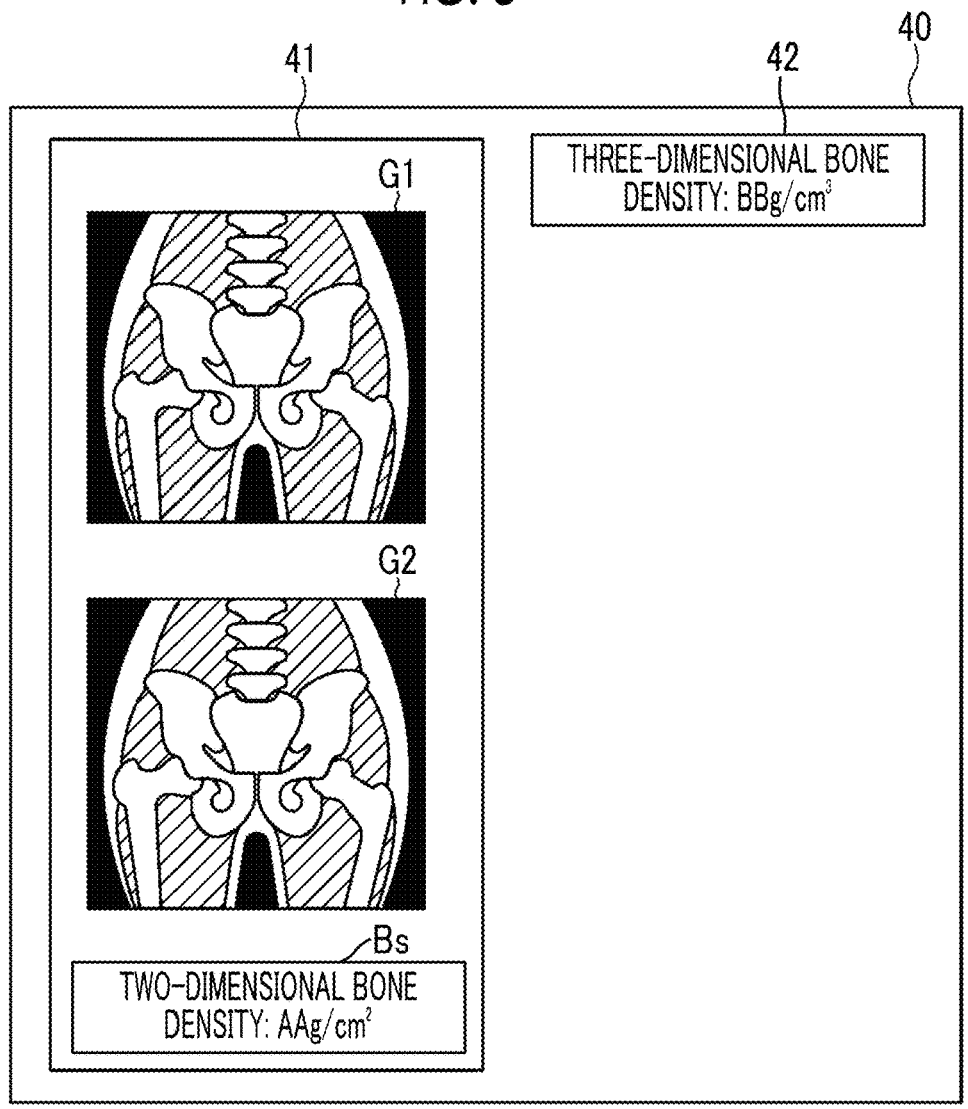
FIG. 5 is a diagram showing teacher data.

FIG. 5 is a diagram showing an example of the teacher data used for training the neural network. As shown in FIG. 5, teacher data 40 consists of learning data 41 and correct answer data 42. In the present embodiment, the data input to the trained neural network 23A in order to obtain the estimation result relating to the three-dimensional bone density is the simple radiation image G0, but the learning data 41 includes two radiation images of the first radiation image G1 and the second radiation image G2 acquired by energy subtraction imaging. In addition, in the present embodiment, the learning data 41 further includes a two-dimensional bone density Bs for the bone part of the subject from which the learning data 41 is acquired.

As the two-dimensional bone density, the bone density per unit area of each pixel of the bone part included in the first radiation image G1 or the second radiation image G2, or a representative value of the bone density per unit area of each pixel included in the region of the target bone of the bone part can be used. In the present embodiment, since the target bone is the femur, the representative value of the bone density per unit area of each pixel included in the femur is used as the two-dimensional bone density Bs.

The correct answer data 42 is the three-dimensional bone density of the target bone (that is, a femur) of the subject from which the learning data 41 is acquired. Note that, in the present embodiment, since the three-dimensional bone density is based on the bone density per unit volume, the unit of the bone density is ($g/cm^3$). On the other hand, since the two-dimensional bone density Bs included in the learning data 41 is based on the bone density per unit area, the unit is ($g/cm^2$). The two-dimensional bone density Bs which is the learning data 41 and the three-dimensional bone density which is the correct answer data 42 are derived by the information derivation device 50. Hereinafter, the information derivation device 50 will be described.

Figure 6:
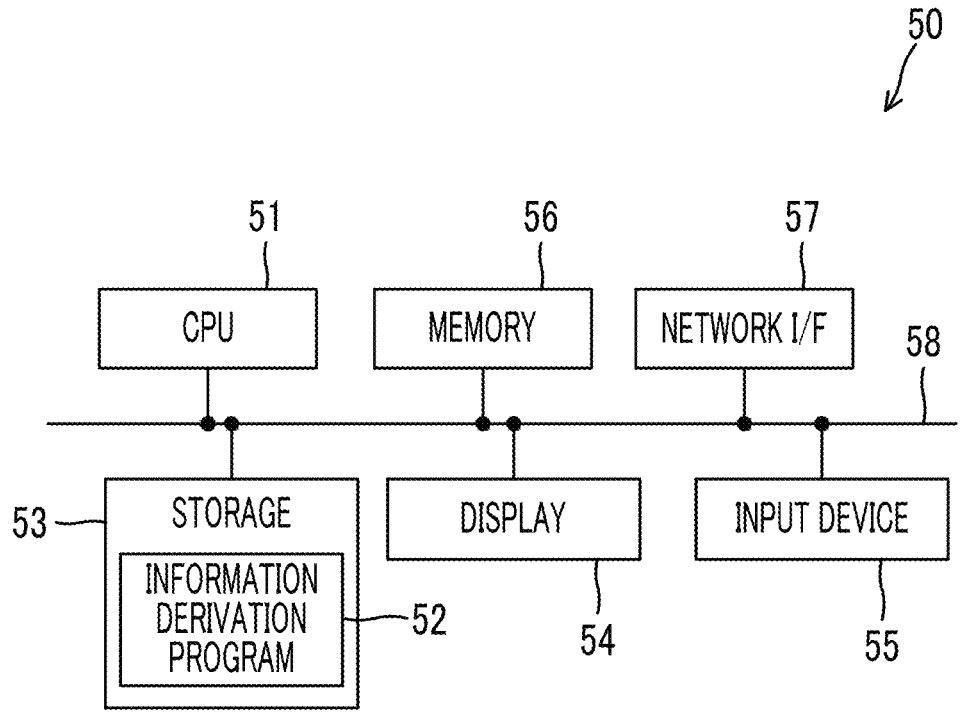
FIG. 6 is a diagram showing a schematic configuration of an information derivation device according to the present embodiment.

FIG. 6 is a schematic block diagram showing a configuration of the information derivation device according to the present embodiment. As shown in FIG. 6, the information derivation device 50 according to the present embodiment is a computer, such as a workstation, a server computer, and a personal computer, and includes a CPU 51, a non-volatile storage 53, and a memory 56 as a transitory storage region. In addition, the information derivation device 50 includes a display 54, such as a liquid crystal display, an input device 55 consisting of a pointing device, such as a keyboard and a mouse, and a network I/F 57 connected to a network (not shown). The CPU 51, the storage 53, the display 54, the input device 55, the memory 56, and the network I/F 57 are connected to a bus 58.

Similar to the storage 13, the storage 53 is realized by the HDD, the SSD, the flash memory, and the like. An information derivation program 52 is stored in the storage 53 as the storage medium. The CPU 51 reads out the information derivation program 52 from the storage 53, expands the read out information derivation program 52 in the memory 56, and executes the expanded information derivation program 52.

Figure 7:
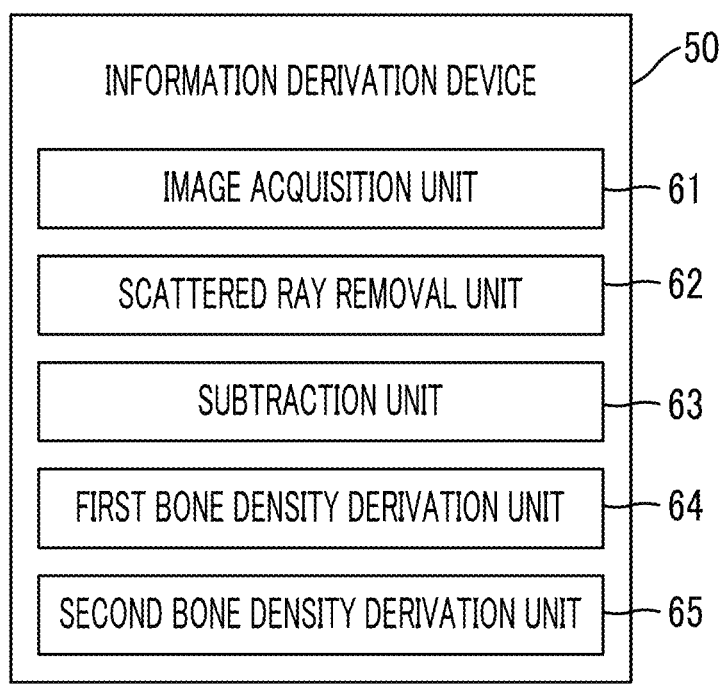
FIG. 7 is a diagram showing a functional configuration of the information derivation device according to the present embodiment.

Then, a functional configuration of the information derivation device according to the present embodiment will be described. FIG. 7 is a diagram showing the functional configuration of the information derivation device according to the present embodiment. As shown in FIG. 7, the information derivation device 50 according to the present embodiment comprises an image acquisition unit 61, a scattered ray removal unit 62, a subtraction unit 63, a first bone density derivation unit 64, and a second bone density derivation unit 65. Further, the CPU 51 executes the information derivation program 52, so that the CPU 51 functions as the image acquisition unit 61, the scattered ray removal unit 62, the subtraction unit 63, the first bone density derivation unit 64, and the second bone density derivation unit 65.

The image acquisition unit 61 acquires the first radiation image G1 and the second radiation image G2, which are the learning data 41, stored in the image storage system 9. Note that the image acquisition unit 61 may acquire the first radiation image G1 and the second radiation image G2 by causing the imaging apparatus 1 to image the subject H in the same manner as the image acquisition unit 21 of the estimation device 10. In addition, the image acquisition unit 61 acquires, from the image storage system 9, the CT image V0 for deriving the learning data 41. Note that the image acquisition unit 61 may acquire the CT image V0 by causing the CT device 8 to image the subject H in the same manner as the image acquisition unit 21 of the estimation device 10.

The image acquisition unit 61 also acquires the imaging conditions in a case in which the first and second radiation images G1 and G2 stored in the image storage system 9 are acquired. The imaging conditions include the imaging dose in a case in which the first radiation image G1 and the second radiation image G2 are acquired, the tube voltage, the SID, the SOD, the presence or absence of the scattered ray removal grid, and the like.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 62 removes the scattered ray component from the first radiation image G1 and the second radiation image G2. For example, the scattered ray removal unit 62 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 62 acquires a virtual model of the subject H having an initial body thickness distribution T0(x,y). The virtual model is data virtually representing the subject H of which a body thickness in accordance with the initial body thickness distribution T0(x,y) is associated with a coordinate position of each pixel of the first radiation image G1. Note that the virtual model of the subject H having the initial body thickness distribution T0(x,y) may be stored in the storage 53 of the information derivation device 50 in advance. In addition, the scattered ray removal unit 62 may calculate a body thickness distribution T(x,y) of the subject H based on the SID and the SOD included in the imaging conditions. In this case, the initial body thickness distribution T0(x,y) can be obtained by subtracting the SOD from the SID.

Next, the scattered ray removal unit 62 generates, based on the virtual model, an image obtained by combining an estimated primary ray image in which a primary ray image obtained by imaging the virtual model is estimated and an estimated scattered ray image in which a scattered ray image obtained by imaging the virtual model is estimated as an estimated image in which the first radiation image G1 obtained by imaging the subject H is estimated.

Next, the scattered ray removal unit 62 corrects the initial body thickness distribution T0(x,y) of the virtual model such that a difference between the estimated image and the first radiation image G1 is small. The scattered ray removal unit 62 repeatedly performs the generation of the estimated image and the correction of the body thickness distribution until the difference between the estimated image and the first radiation image G1 satisfies a predetermined termination condition. The scattered ray removal unit 62 derives the body thickness distribution in a case in which the termination condition is satisfied as the body thickness distribution T(x,y) of the subject H. In addition, the scattered ray removal unit 62 removes the scattered ray component included in the first radiation image G1 by subtracting the scattered ray component in a case in which the termination condition is satisfied from the first radiation image G1.

Figure 8:
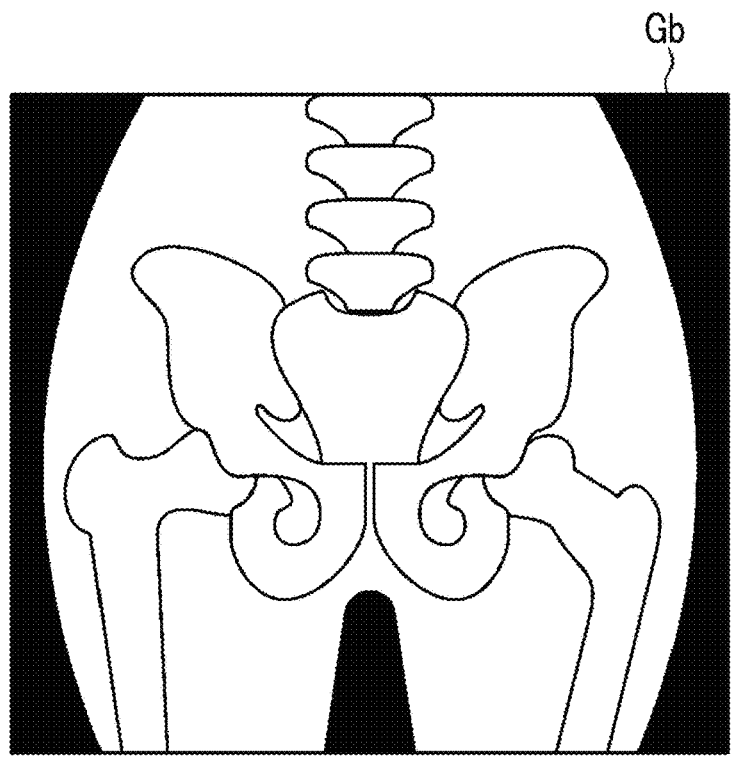
FIG. 8 is a diagram showing a bone part image.

The subtraction unit 63 derives a bone part image Gb obtained by extracting the bone part of the subject H from the first and second radiation images G1 and G2 by performing the energy subtraction processing. Note that, in the first and second radiation images G1 and G2 in the subsequent processing, the scattered ray component is removed. In a case in which the bone part image Gb is derived, the subtraction unit 63 performs weighting subtraction between the corresponding pixels with respect to the first and second radiation images G1 and G2 as shown in Expression (1) to generate the bone part image Gb in which the bone part of the subject H included in each of the radiation images G1 and G2 is extracted, as shown in FIG. 8. In Expression (1), α is a weighting coefficient. In addition, the pixel value of each pixel in the bone region of the bone part image Gb is a bone part pixel value.

$$Gb(x,y)=\alpha \cdot G2(x,y)-G1(x,y) \quad (1)$$

The first bone density derivation unit 64 derives the bone density for each pixel of the bone part image Gb. In the present embodiment, the first bone density derivation unit 64 derives the bone density by converting each pixel value of the bone part image Gb into the pixel value of the bone part image acquired under a standard imaging condition. Specifically, the first bone density derivation unit 64 derives the bone density by correcting each pixel value of the bone part image Gb by using a correction coefficient acquired from a look-up table described below.

Here, a contrast between the soft part and the bone part in the radiation image is lower as the tube voltage in the radiation source 3 is higher and the energy of the radiation emitted from the radiation source 3 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 9:
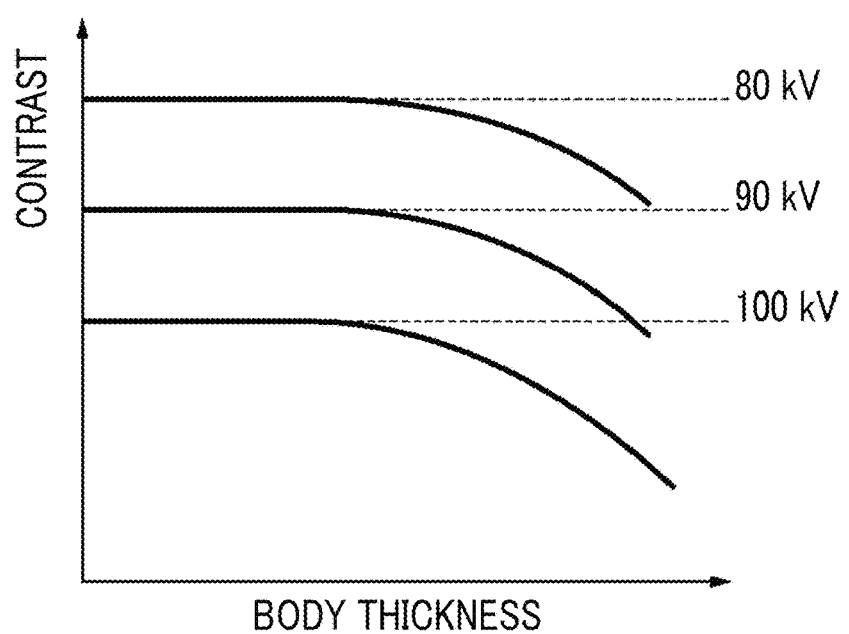
FIG. 9 is a diagram showing a relationship of a contrast between a bone part and a soft part with respect to a body thickness of a subject.

FIG. 9 is a diagram showing a relationship of the contrast between the bone part and the soft part with respect to the body thickness of the subject H. Note that FIG. 9 shows the relationship of the contrast between the bone part and the soft part with respect to the body thickness of the subject H at the three tube voltages of 80 kV, 90 kV, and 100 kV. As shown in FIG. 9, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 9 shifts to a higher contrast side as the pixel value of the bone region in the bone part image Gb is increased.

In the present embodiment, the look-up table for acquiring the correction coefficient for correcting the difference in the contrast depending on the tube voltage at the time of imaging and the reduction in the contrast due to the influence of the beam hardening in the bone part image Gb is stored in the storage 53 of the information derivation device 50. The correction coefficient is the coefficient for correcting each pixel value of the bone part image Gb.

Figure 10:
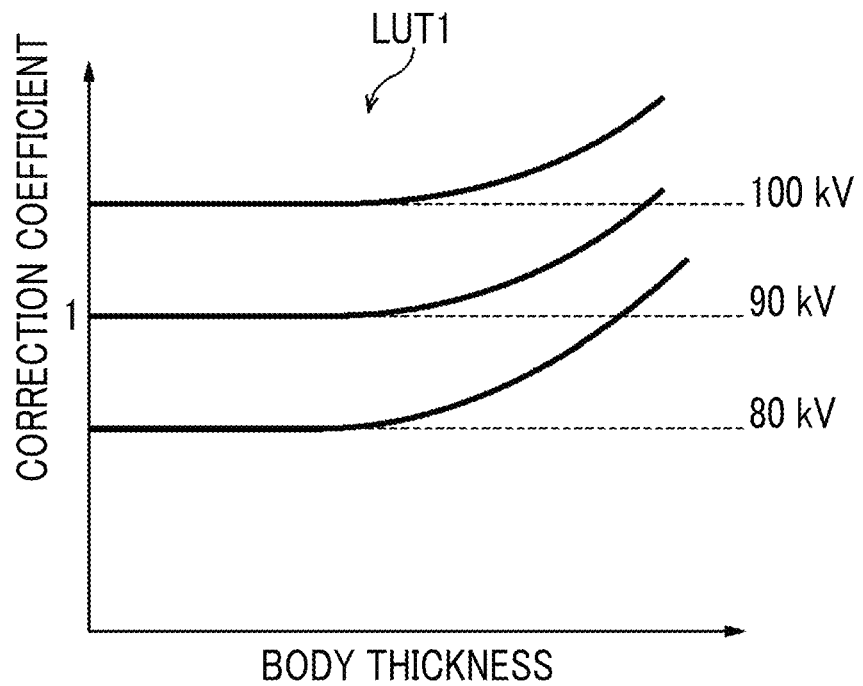
FIG. 10 is a diagram showing an example of a look-up table for acquiring a correction coefficient.

FIG. 10 is a diagram showing an example of the look-up table for acquiring the correction coefficient. In FIG. 10, a look-up table (hereinafter simply referred to as a table) LUT1 in which the standard imaging condition is set to the tube voltage of 90 kV is shown. As shown in FIG. 10, in the table LUT1, the correction coefficient is set to be larger as the tube voltage is higher and the body thickness of the subject H is larger. In the example shown in FIG. 10, since the standard imaging condition is the tube voltage of 90 kV, the correction coefficient is 1 in a case in which the tube voltage is 90 kV and the body thickness is 0. Note that, although the table LUT1 is shown in two dimensions in FIG. 10, the correction coefficient differs depending on the pixel value of the bone region. Therefore, the table LUT1 is actually a three-dimensional table to which an axis representing the pixel value of the bone region is added.

The first bone density derivation unit 64 extracts the body thickness distribution T(x,y) of the subject H and a correction coefficient C0(x,y) for each pixel depending on the imaging condition including a set value of the tube voltage stored in the storage 13 from the table LUT1. Moreover, as shown in Expression (2), the first bone density derivation unit 64 multiplies each pixel (x,y) of the bone region in the bone part image Gb by the correction coefficient C0(x,y) to derive the two-dimensional bone density Bs(x,y) (g/cm$^2$) for bone density per unit area for each pixel of the bone part image Gb. The two-dimensional bone density Bs(x,y) derived in this way is acquired by imaging the subject H by the tube voltage of 90 kV, which is the standard imaging condition, and represents the pixel value of the bone region included in the radiation image from which the influence of the beam hardening is removed. Therefore, a bone density image in which the derived bone density is used as the pixel value of each pixel is derived by the first bone density derivation unit 64.

$$Bs(x,y)=C0(x,y)\times Gb(x,y) \qquad (2)$$

Moreover, in the present embodiment, the first bone density derivation unit 64 derives the representative value of the two-dimensional bone density Bs only for the target bone. For example, in a case in which the target bone is the femur, the first bone density derivation unit 64 derives the representative value of the two-dimensional bone density Bs of the femur region by deriving the representative value of the two-dimensional bone density Bs of each pixel in the femur region in the bone part image Gb. An average value, a median value, a minimum value, a maximum value, and the like can be used as the representative value. In the present embodiment, the representative value of the two-dimensional bone density Bs of the femur which is the target bone is used as the two-dimensional bone density Bs of the learning data 41.

Figure 11:
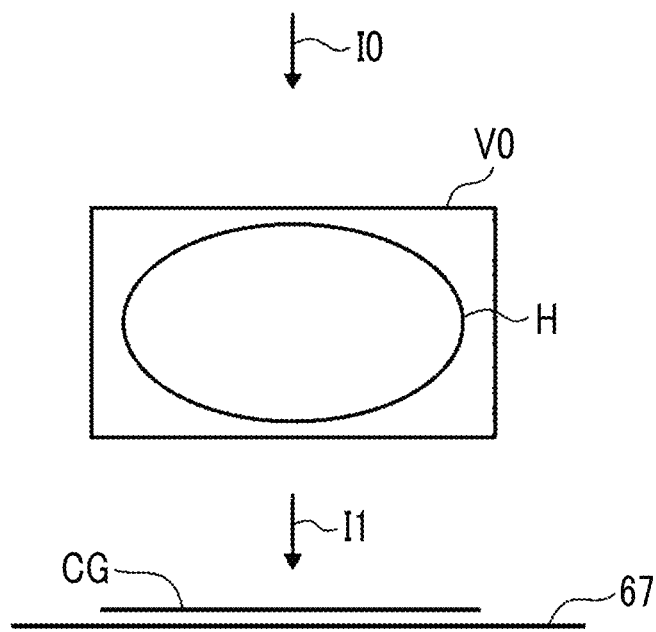
FIG. 11 is a diagram for describing the derivation of a three-dimensional bone density.

The second bone density derivation unit 65 derives the three-dimensional bone density from the CT image V0. FIG. 11 is a diagram for describing the derivation of the three-dimensional bone density. Note that, in FIG. 11, the three-dimensional CT image V0 is shown in two dimensions for the sake of description. As shown in FIG. 11, the subject H is included in a three-dimensional space represented by the CT image V0. The subject H consists of a plurality of compositions of the bone part, the fat, the muscle, and the internal organs.

Here, the CT value V0(x, y, z) in each pixel of the CT image V0 can be represented by Expression (3) by using an attenuation coefficient pi of the composition in the pixel and an attenuation coefficient μw of water. (x, y, z) are coordinates representing pixel positions of the CT image V0. Note that, in the following description, the attenuation coefficient means the linear attenuation coefficient unless otherwise specified. The attenuation coefficient represents a degree (ratio) of the radiation attenuation due to absorption or scattering. The attenuation coefficient differs depending on a specific composition (density or the like) and the thickness (mass) of the structure through which radiation is transmitted.

$$V0(x, y, z)=(\mu i-\mu w)/\mu w\times 1000 \qquad (3)$$

The attenuation coefficient μw of the water is known. Therefore, by solving Expression (3) for μi, the attenuation coefficient μi of each composition can be calculated as shown in Expression (4).

$$\mu i=V0(x, y, z)\times \mu w/1000+\mu w \qquad (4)$$

As shown in FIG. 11, in a case in which the three-dimensional bone density is derived, the second bone density derivation unit 65 virtually irradiates the subject H with the radiation having an irradiation dose I0 from the front side of the subject H, and derives the composite two-dimensional image CG obtained by virtually detecting the radiation transmitted through the subject H by the radiation detector (not shown) installed on a virtual plane 67. Note that the irradiation dose I0 of the virtual radiation and the radiation energy are set depending on predetermined imaging conditions. Specifically, the irradiation dose I0 need only be set by preparing a table corresponding to the imaging conditions, such as the tube voltage, the mAs value, and the SID, and referring to the table. In addition, the radiation energy need only be set by preparing the table depending on the tube voltage and referring to the table. In this case, a reaching dose I1(x,y) for each pixel of the composite two-dimensional image CG is transmitted through one or more compositions in the subject H. Therefore, the reaching dose I1(x,y) can be derived by Expression (5) by using the attenuation coefficient pi of one or more compositions through which the radiation of the irradiation dose I0 is transmitted. Note that the reaching dose I1(x,y) is the pixel value of each pixel of the composite two-dimensional image CG.

$$I1(x,y)=I0\times \exp(-\int \mu i \cdot dt) \qquad (5)$$

Figure 12:
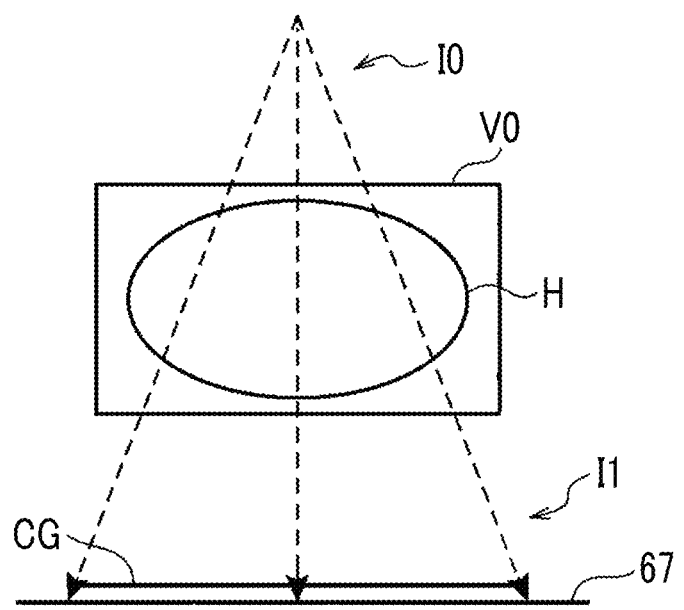
FIG. 12 is a diagram for describing the derivation of the three-dimensional bone density.

Note that, in a case in which it is assumed that the radiation source to emit the radiation is a plane light source, as the attenuation coefficient pi used in Expression (5), a value derived from the CT value of the pixels arranged in the vertical direction shown in FIG. 11 by Expression (4) need only be used. In addition, in a case in which it is assumed that the plane light source of the light source to emit the radiation is a point light source, as shown in FIG. 12, based on the geometric positional relationship between the point light source and each position on the virtual plane 67, the pixel on the path of the radiation reaching each pixel need only be specified and the attenuation coefficient pi derived from the CT value of the specified pixel by Expression (4) need only be used.

In addition, the composite two-dimensional image CG is derived based on the radiation virtually emitted from the front side of the subject H. Therefore, the composite two-dimensional image CG can associate the positions with the first and second radiation images G1 and G2, and further with the bone part image Gb. Therefore, the second bone density derivation unit 65 performs registration between the composite two-dimensional image CG and the bone part image Gb, and associates the corresponding pixel positions with each other.

Figure 13:
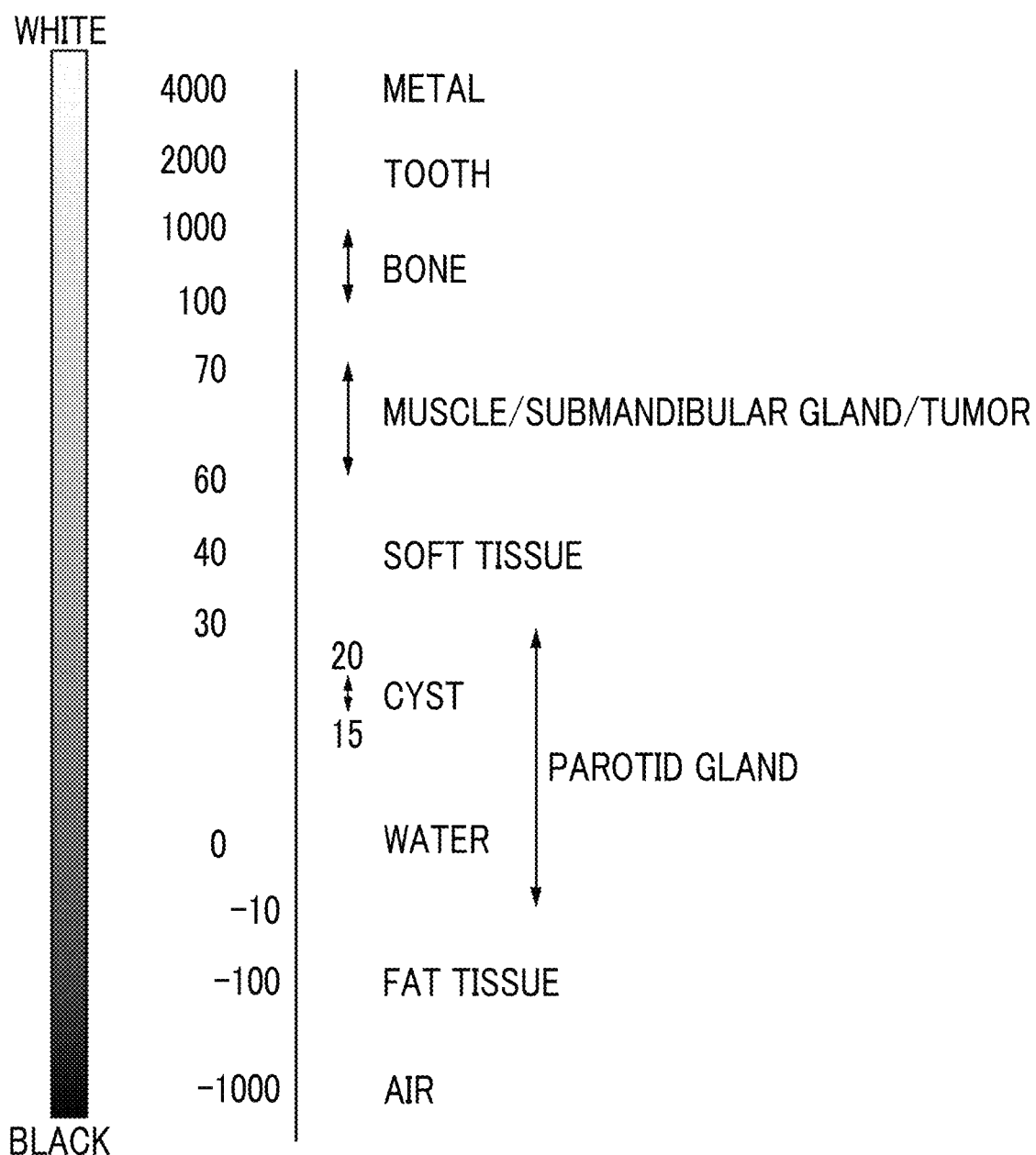
FIG. 13 is a diagram for describing a CT value.

The second bone density derivation unit 65 derives the three-dimensional bone density By of the subject H for each pixel of the composite two-dimensional image CG by using the CT image V0. Here, description for the CT value will be made. FIG. 13 is a diagram for describing the CT value. The CT value is a numerical value of the X-ray absorbance in the human body. Specifically, as shown in FIG. 13, the CT value is determined depending on the composition constituting the human body, such as 0 for the water and −1000 (unit: HU) for the CT value of the air.

The second bone density derivation unit 65 first specifies the bone region in the CT image V0 based on the CT value of the CT image V0. Specifically, the region consisting of the pixels having the CT value of 100 to 1000 is specified as the bone region by the threshold value processing. Note that the bone region may be specified by using the trained neural network that is trained to detect the bone region from the CT image V0 instead of the threshold value processing. In addition, the bone region may be specified by displaying the CT image V0 on the display 54 and receiving designation of the bone region by a manual operation in the displayed CT image V0.

Here, the density $\rho$ (g/cm$^3$) per unit volume of the composition in each pixel of the CT image V0 can be derived by Expression (6) from the attenuation coefficient $\mu i$ (1/cm) of the composition and the mass attenuation coefficient $\mu e$ (cm$^2$/g) of the composition.

$$\rho = \mu i / \mu e \tag{6}$$

Figure 14:
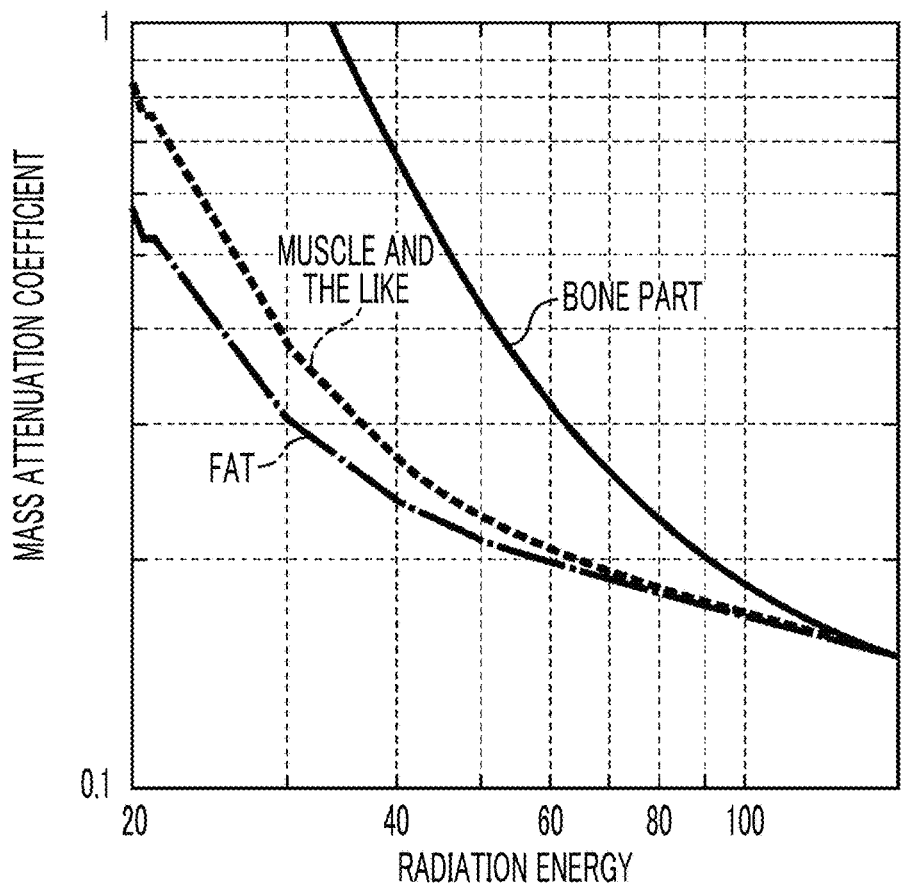
FIG. 14 is a diagram showing a relationship between radiation energy and a mass attenuation coefficient.

FIG. 14 is a diagram showing a relationship between the radiation energy and the mass attenuation coefficient in various compositions of the human body. FIG. 14 shows the relationship between the radiation energy and the mass attenuation coefficient for the bone part, the muscle and the like, and the fat. Note that the muscle and the like mean the muscle, the blood, and the water. In the present embodiment, the relationship between the radiation energy and the mass attenuation coefficient, which is shown in FIG. 14, is stored in the storage 53 as a table. In the present embodiment, since the mass attenuation coefficient of the bone part is required, the mass attenuation coefficient of the bone part is acquired by referring to the relationship of the bone part in the table shown in FIG. 14 based on the virtual radiation energy. In addition, the attenuation coefficient $\mu b$ in each pixel of the bone region is derived by Expression (4). Further, the bone density $\rho$ per unit volume in each pixel of the bone region included in the CT image V0 is derived by Expression (6).

Note that the CT image V0 is the three-dimensional image, the unit of the bone density $\rho$ per unit volume derived by Expression (6) is (g/cm$^3$). In the present embodiment, the second bone density derivation unit 65 derives the bone density per unit volume for each pixel of the composite two-dimensional image CG as the three-dimensional bone density Bv. Therefore, the second bone density derivation unit 65 projects the bone density $\rho$ per unit volume derived by Expression (6) onto the virtual plane 67 in the same manner as in a case in which the composite two-dimensional image CG is derived to derive the three-dimensional bone density Bv for each pixel of the composite two-dimensional image CG. The unit of the three-dimensional bone density Bv is (g/cm$^3$).

Note that, in a case of projection, the representative value of the bone density per unit volume of each pixel of the CT image V0 on the path reaching each pixel of the composite two-dimensional image CG from the virtual radiation source need only be derived. An integrated value, an average value, a maximum value, a median value, a minimum value, and the like can be used as the representative value. Moreover, in the present embodiment, the second bone density derivation unit 65 derives the representative value of the three-dimensional bone density Bv only for the target bone. For example, in the present embodiment, since the target bone is the femur, the second bone density derivation unit 65 derives the representative value of the three-dimensional bone density Bv of the femur region by deriving the representative value of the three-dimensional bone density Bv of each pixel of the femur region in the composite two-dimensional image CG. An average value, a median value, a minimum value, a maximum value, and the like can be used as the representative value. In the present embodiment, the representative value of the three-dimensional bone density Bv of the femur, which is the target bone, is used as the correct answer data 42. As a result, the two-dimensional bone density Bs derived by the first bone density derivation unit 64 and the three-dimensional bone density Bv derived by the second bone density derivation unit 65 are the two-dimensional bone density and the three-dimensional bone density for the same target bone, respectively.

The two-dimensional bone density used as the learning data 41 and the three-dimensional bone density used as the correct answer data 42 are derived at the same time as the acquisition of the learning data 41, and are transmitted to the image storage system 9. In the image storage system 9, the learning data 41 and the correct answer data 42 are stored in association with each other as the teacher data 40. Note that, in order to improve the robustness of the learning, the teacher data 40 including, as learning data 41, an image obtained by performing at least one of enlargement/reduction, contrast change, movement, in-plane rotation, inversion, or noise addition on the same image may be additionally created and stored.

Figure 15:
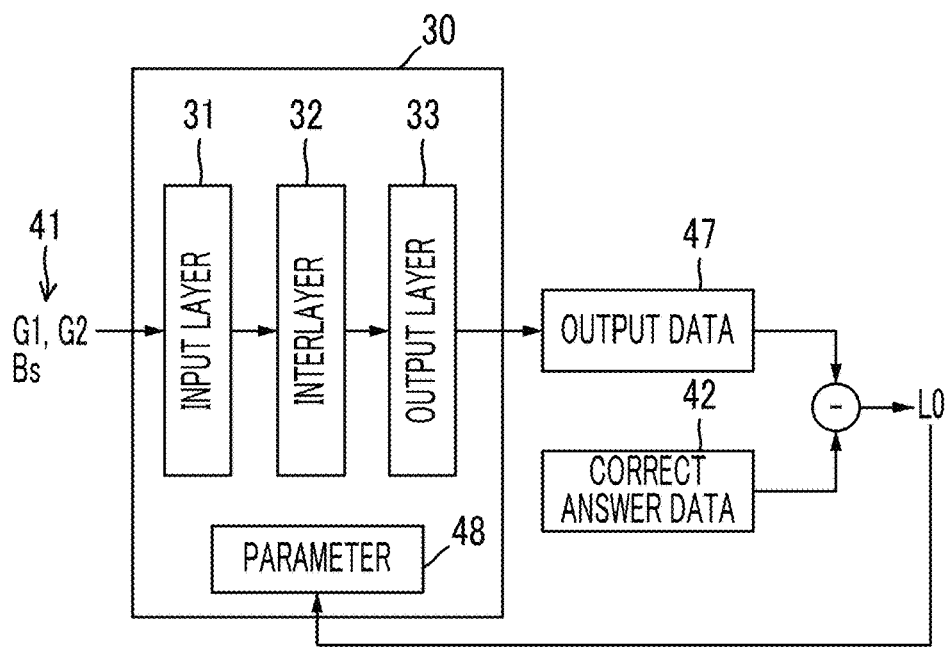
FIG. 15 is a diagram for describing learning of the neural network.

The description will be returned to the estimation device 10. The learning unit 24 trains the neural network using a large amount of the teacher data 40. FIG. 15 is a diagram for describing learning of the neural network 30. In a case in which the neural network 30 learns, the learning unit 24 inputs the learning data 41, that is, the first and second radiation images G1 and G2, and the two-dimensional bone density Bs to the input layer 31 of the neural network 30. Further, the learning unit 24 outputs the three-dimensional bone density of the target bone as output data 47 from the output layer 33 of the neural network 30. Further, the learning unit 24 derives a difference between the output data 47 and the correct answer data 42 as a loss L0.

The learning unit 24 trains the neural network 30 based on the loss L0. Specifically, the learning unit 24 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 24 repeats the adjustment of the parameter 48 until the loss L0 is equal to or smaller than a predetermined threshold value. As a result, in a case in which the simple radiation image G0 is input, the parameter 48 is adjusted so as to output the bone density of the target bone, and the trained neural network 23A is constructed. The constructed trained neural network 23A is stored in the storage 13.

Figure 16:
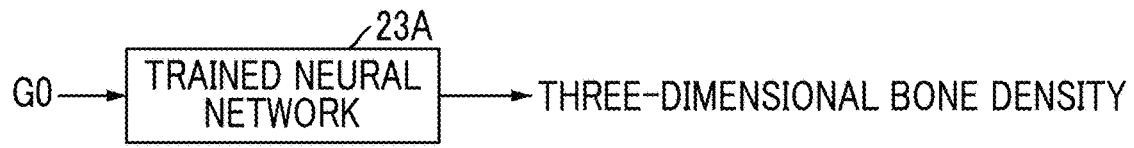
FIG. 16 is a conceptual diagram of processing performed by a trained neural network.

FIG. 16 is a conceptual diagram of processing performed by the trained neural network 23A. As shown in FIG. 16, in a case in which the simple radiation image G0 of a patient is input to the trained neural network 23A constructed as described above, the trained neural network 23A outputs the three-dimensional bone density for the target bone (that is, the femur) included in the input simple radiation image G0.

Figure 17:
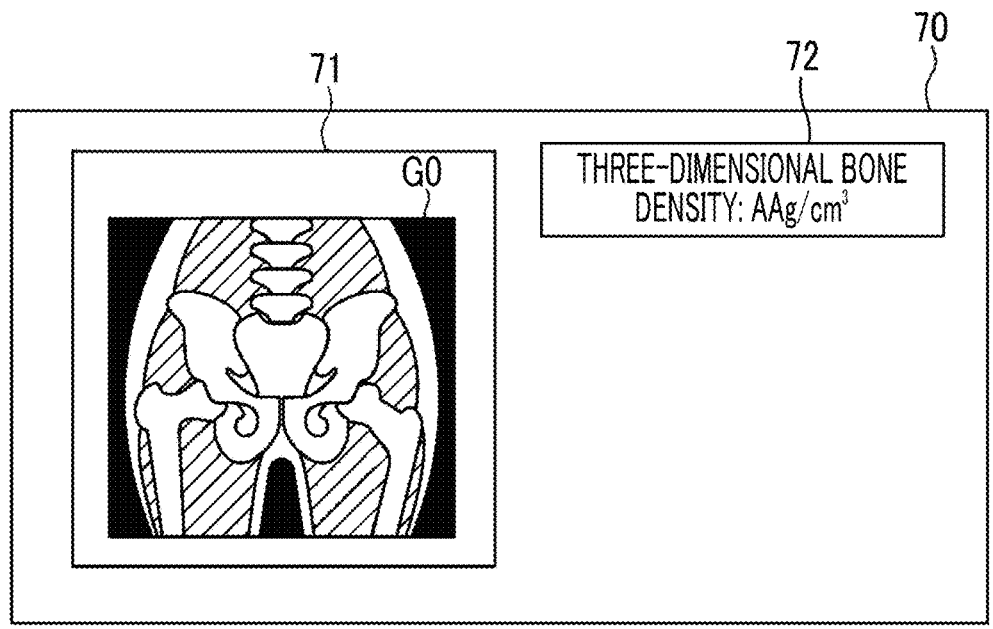
FIG. 17 is a diagram showing a display screen of an estimation result.

The display controller 25 displays the estimation result of the bone density estimated by the estimation unit 23 on the display 14. FIG. 17 is a diagram showing a display screen of the estimation result. As shown in FIG. 17, a display screen 70 has an image display region 71 and a bone density display region 72. The simple radiation image G0 of the subject H is displayed in the image display region 71. In addition, in the bone density display region 72, the representative value of the three-dimensional bone density in the vicinity of the joint of the femur in the bone density estimated by the estimation unit 23 is displayed.

Figure 18:
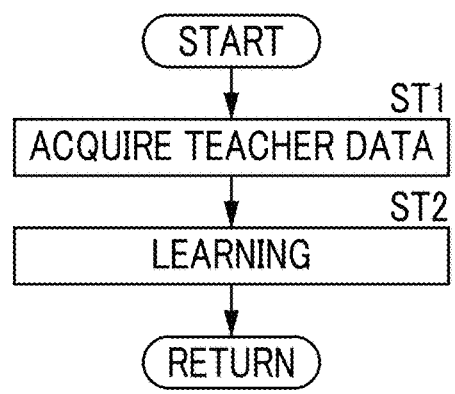
FIG. 18 is a flowchart of learning processing performed in the present embodiment.

Then, processing performed in the present embodiment will be described. FIG. 18 is a flowchart showing learning processing performed in the present embodiment. First, the information acquisition unit 22 acquires the teacher data 40 from the image storage system 9 (step ST1), and the learning unit 24 inputs the learning data 41 included in the teacher data 40 to the neural network 30 to output the three-dimensional bone density and trains the neural network 30 using the loss L0 based on the difference from the correct answer data 42 (step ST2), and the processing returns to step ST1. Further, the learning unit 24 repeats the processing of steps ST1 and ST2 until the loss L0 reaches the predetermined threshold value, and terminates the learning processing. Note that the learning unit 24 may terminate the learning processing by repeating the learning a predetermined number of times. As a result, the learning unit 24 constructs the trained neural network 23A.

Figure 19:
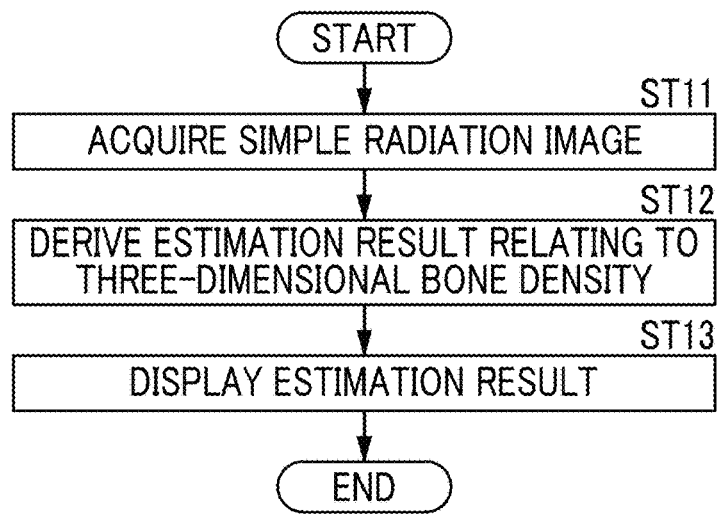
FIG. 19 is a flowchart showing estimation processing performed in the present embodiment.

Then, estimation processing according to the present embodiment will be described. FIG. 19 is a flowchart showing the estimation processing according to the present embodiment. Note that the simple radiation image G0 is acquired by the imaging and stored in the storage 13. In a case in which an instruction for starting the processing is input from the input device 15, the image acquisition unit 21 acquires the simple radiation image G0 from the storage 13 (step ST11). Then, the estimation unit 23 derives the estimation result relating to the three-dimensional bone density from the simple radiation image G0 (step ST12). Further, the display controller 25 displays the estimation result relating to the three-dimensional bone density derived by the estimation unit 23 on the display 14 together with the simple radiation image G0 (step ST13), and terminates the processing.

As described above, in the present embodiment, the estimation result relating to the three-dimensional bone density of the subject H included in the simple radiation image G0 is derived by using the trained neural network 23A constructed by performing learning using the first and second radiation images G1 and G2, and the two-dimensional bone density Bs as the teacher data. Here, in the present embodiment, the two radiation images, the first and second radiation images G1 and G2, are used for training the neural network. Further, in the present embodiment, the two-dimensional bone density Bs is also used for training the neural network. Therefore, the trained neural network 23A can derive the estimation result relating to the three-dimensional bone density from the simple radiation image G0 with higher accuracy as compared with a case in which one radiation image and the information relating to the bone density are used as the teacher data. Therefore, according to the present embodiment, the estimation result relating to the three-dimensional bone density can be derived with higher accuracy.

Note that, in the embodiment described above, the second bone density derivation unit 65 projects the bone density per unit volume for each pixel of the CT image V0 onto each pixel of the composite two-dimensional image CG to derive the three-dimensional bone density, but the present disclosure is not limited to this. The representative value of the bone density ρ of each pixel of the three-dimensional region of the target bone in the CT image V0 derived by Expression (6) may be derived as the three-dimensional bone density of the region of the target bone. An average value, a median value, a minimum value, a maximum value, and the like of the bone density ρ of each pixel can be used as the representative value. In this case, the bone density for each pixel of the composite two-dimensional image CG derived by the second bone density derivation unit 65 in the embodiment described above may be used as the two-dimensional bone density Bs in the learning data 41.

Figure 20:
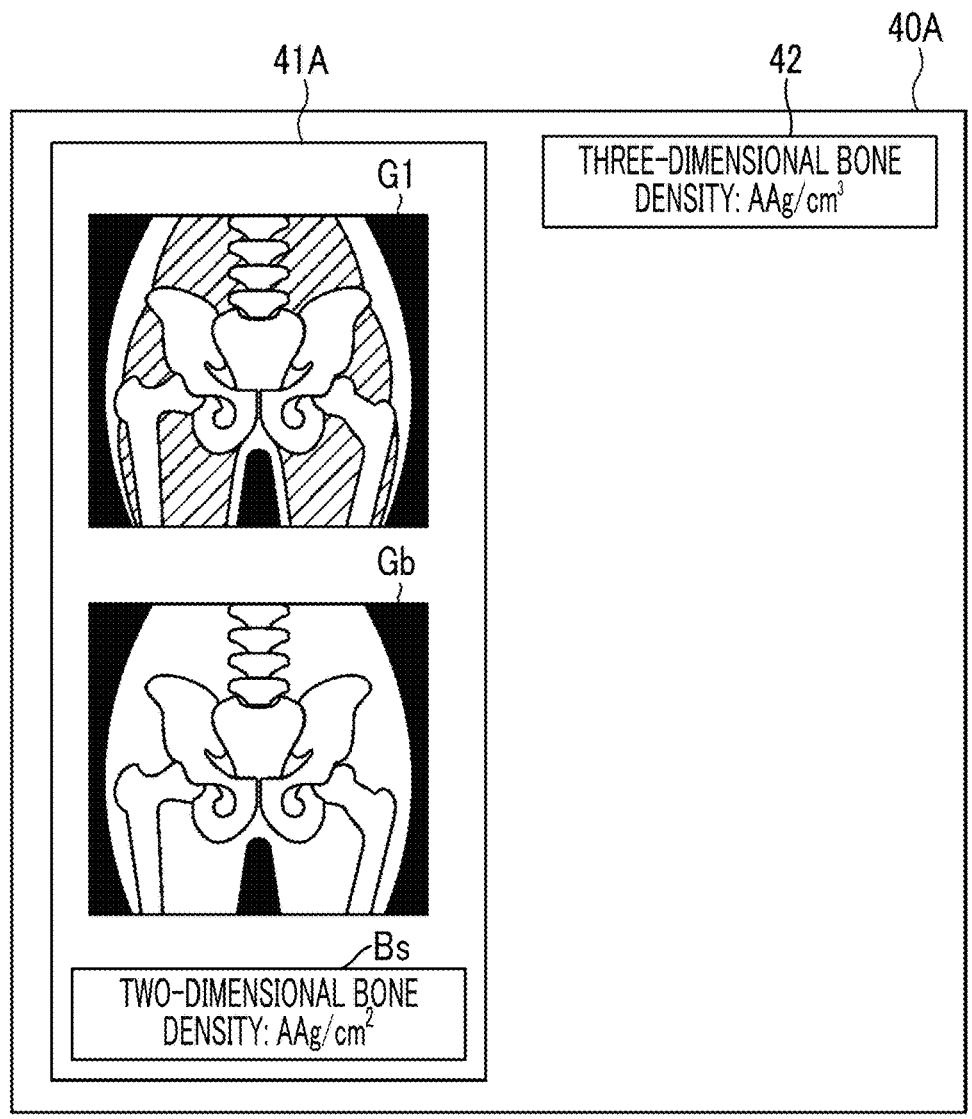
FIG. 20 is a diagram showing another example of the teacher data.

In addition, in the embodiment described above, the first and second radiation images G1 and G2 are used as the learning data 41 of the teacher data 40, but the present disclosure is not limited to this. As in the teacher data 40A shown in FIG. 20, the bone part image Gb may be used as learning data 41A instead of the second radiation image G2. In this case, the bone part image Gb need only be derived from the embodiment described above.

Figure 21:
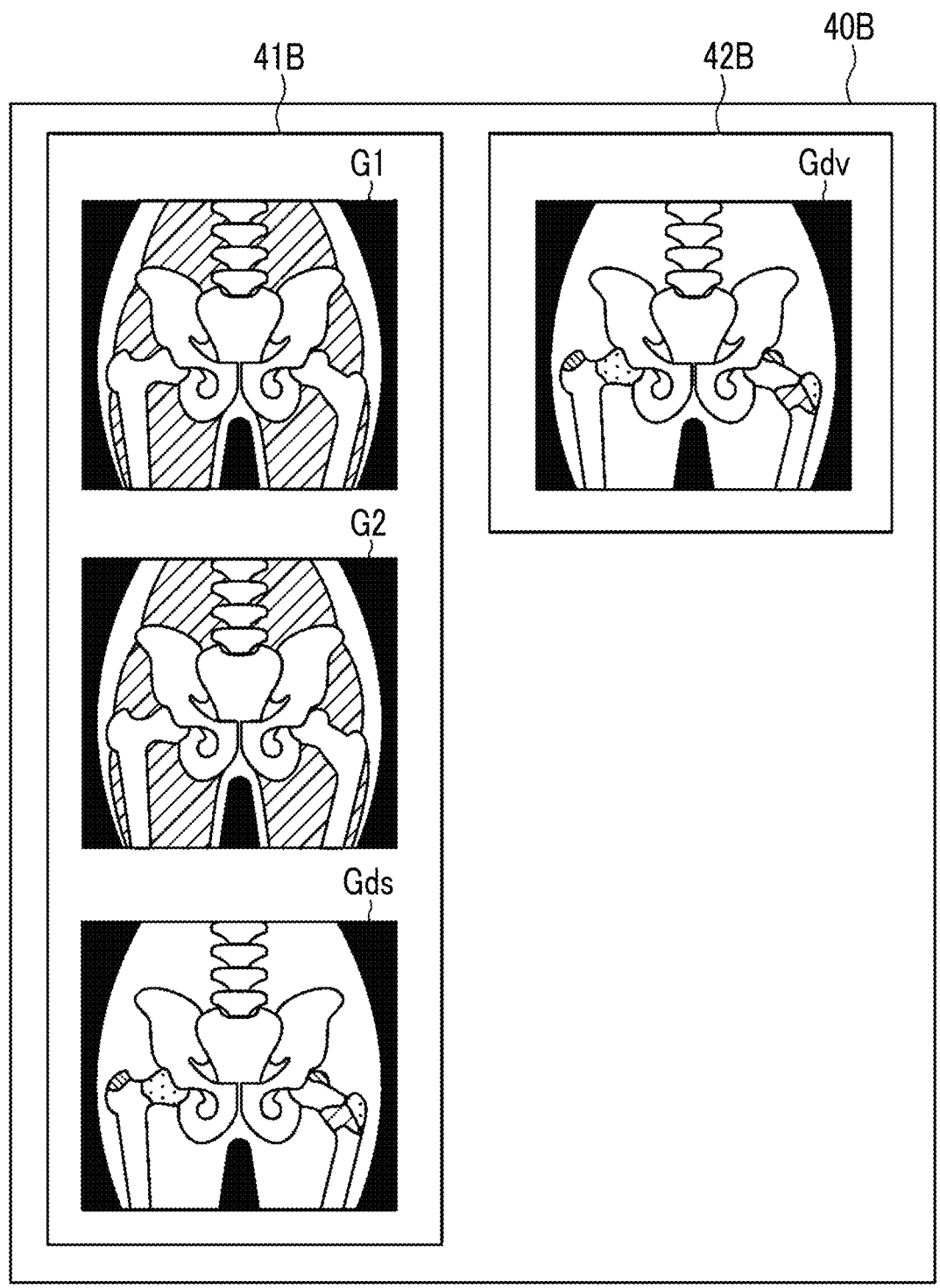
FIG. 21 is a diagram showing still another example of the teacher data.

In addition, in the embodiment described above, as in teacher data 40B shown in FIG. 21, instead of the representative value of the two-dimensional bone density Bs, a two-dimensional bone density image Gds in which each pixel is the value of the two-dimensional bone density may be used as learning data 41B. In this case, a three-dimensional bone density image Gdv in which each pixel is the value of the three-dimensional bone density need only be used as the correct answer data 42. In a case in which such teacher data 40B is used, the estimation unit 23 of the estimation device 10 derives the three-dimensional bone density image from the simple radiation image G0 as the estimation result relating to the three-dimensional bone density. In this way, in a case in which the three-dimensional bone density image is derived, the bone density image may be displayed on the display screen.

Figure 22:
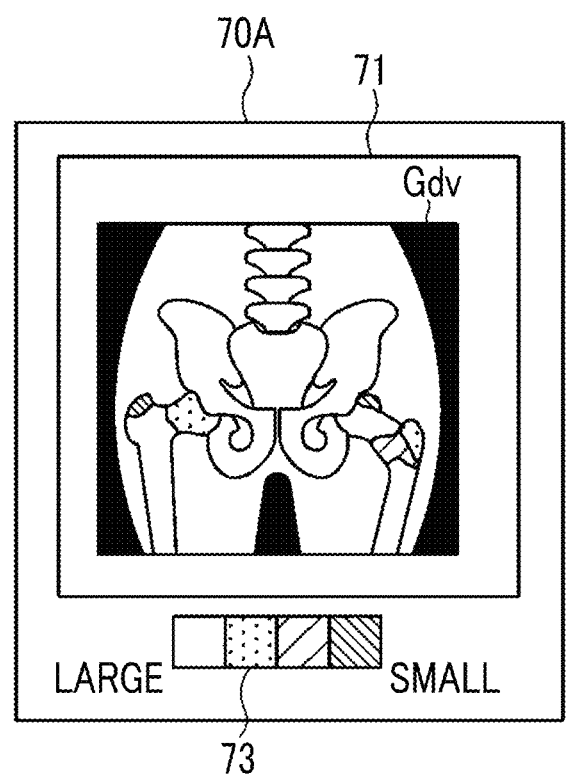
FIG. 22 is a diagram showing another example of the display screen of the estimation result.

FIG. 22 is a diagram showing another example of the display screen of the estimation result. As shown in FIG. 22, a display screen 70A has the image display region 71 similar to the display screen 70 shown in FIG. 17. In the image display region 71, the three-dimensional bone density image Gdv, which is the estimation result of the three-dimensional bone density in the simple radiation image G0 of the subject H, is displayed. In the three-dimensional bone density image Gdv, a pattern is added to the bone region depending on the three-dimensional bone density. Note that, in FIG. 22, for the sake of simplicity, the pattern representing the bone mineral density is added only to the femur. Below the image display region 71, a reference 73 representing the magnitude of the bone mineral density for the added pattern is displayed. The operator can easily recognize the three-dimensional bone density of the patient by interpreting the three-dimensional bone density image Gdv with reference to the reference 73. Note that different colors may be added to the three-dimensional bone density image Gdv depending on the three-dimensional bone density instead of the pattern.

In addition, in the embodiment described above, the information relating to the three-dimensional bone density of the femur in the vicinity of the hip joint is estimated, but the target bone is not limited to the femur. The technology of the present disclosure can also be applied in estimating the information relating to the three-dimensional bone density for any bone part, such as the femur and tibia in the vicinity of a knee joint, a vertebra, such as a lumbar vertebra, a heel bone, and a metacarpal bone.

In addition, in the embodiment described above, the estimation result relating to the bone density is derived from the simple radiation image G0, but the present disclosure is not limited to this. For example, also in a case in which the estimation result relating to the bone density is derived from the DXA scanning image acquired by imaging the subject with a DXA imaging apparatus disclosed in JP-H9-108206A (JP1997-108206A) and JP2006-271437A, the technology of the present disclosure can be applied. The DXA scanning image is the radiation image captured by the radiation detector by irradiating the subject while switching between a finely collimated high-energy radiation beam and a low-energy radiation beam and scanning. The finely collimated radiation beam is, for example, a radiation beam formed into a pencil beam, a narrow fan beam, a wide fan beam, or the like by using a collimator positioned between the radiation source and the subject. The low-energy radiation refers to radiation with a relatively lower energy than the high-energy radiation.

In addition, the trained neural network 23A may be constructed by using the DXA scanning image as a teacher image. In this case, for example, the DXA scanning image acquired by the low-energy radiation beam and the DXA scanning image acquired by the high-energy radiation beam need only be used instead of the first and second radiation images G1 and G2 shown in FIG. 5. In addition, the two-dimensional bone density obtained from the DXA scanning image need only be used as the two-dimensional bone density Bs. In addition, instead of the first radiation image G1 and bone part image Gb shown in FIG. 21, the bone part image obtained from the DXA scanning image and the DXA scanning image acquired by the low-energy radiation beam need only be used.

In addition, in the embodiment described above, the two-dimensional bone density of the learning data is derived by the energy subtraction processing, but the present disclosure is not limited to this. The two-dimensional bone density may be derived by the DXA method using the DXA scanning image acquired at the same time as the acquisition of the first and second radiation images G1 and G2 included in the learning data.

In addition, in the embodiment described above, the estimation device 10 trains the neural network to construct the trained neural network 23A, but the present disclosure is not limited to this. The trained neural network 23A constructed in a device other than the estimation device 10 may be used for the estimation unit 23 of the estimation device 10 according to the present embodiment.

In addition, in the embodiment described above, the first and second radiation images G1 and G2 are acquired by the one-shot method in a case in which the energy subtraction processing is performed for deriving the bone density, but the present disclosure is not limited to this. The first and second radiation images G1 and G2 may be acquired by a so-called two-shot method in which imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed.

As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in the embodiment described above, the derivation of the bone density as the correct answer data of the teacher data and the estimation processing of the information relating to the bone density are performed by using the radiation image acquired by the system that images the subject H by using the first and second radiation detectors 5 and 6, it is needless to say that the technology of the present disclosure can be applied to even in a case in which the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation according to the embodiment described above is not particularly limited, and $\alpha$-rays or $\gamma$-rays can be used in addition to X-rays.

In addition, in the embodiment described above, various processors shown below can be used as the hardware structures of processing units that execute various pieces of processing, such as the image acquisition unit 21, the information acquisition unit 22, the estimation unit 23, the learning unit 24, and the display controller 25 of the estimation device 10, and the image acquisition unit 61, the scattered ray removal unit 62, the subtraction unit 63, the first bone density derivation unit 64, and the second bone density derivation unit 65 of the information derivation device 50. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. An estimation device comprising:
at least one processor,
wherein the processor functions as a trained neural network that derives an estimation result relating to a three-dimensional bone density of a bone part from a simple radiation image acquired by simply imaging a subject including the bone part, or a DXA scanning image acquired by imaging the subject by a DXA method, and the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image of the subject or a bone part image representing the bone part of the subject, the two-dimensional bone density of the bone part included in the radiation image, the DXA scanning image, or the bone part image, and the three-dimensional bone density of the bone part of the subject.

2. The estimation device according to claim 1, wherein the three-dimensional bone density is derived from a three-dimensional image of the subject.

3. The estimation device according to claim 2, wherein the three-dimensional image is a CT image.

4. The estimation device according to claim 3, wherein the three-dimensional bone density is obtained by specifying a bone region in the CT image, deriving an attenuation coefficient of radiation in the bone region, and deriving the three-dimensional bone density based on a bone density at each position in the bone region, which is derived based on the attenuation coefficient of the radiation and a mass attenuation coefficient in the bone region.

5. The estimation device according to claim 1, wherein the two-dimensional bone density is derived from the two radiation images or the DXA scanning image.

6. The estimation device according to claim 5, wherein the two-dimensional bone density is derived based on a body thickness distribution of the subject estimated based on at least one radiation image of the two radiation images or the DXA scanning image, an imaging condition in a case of acquiring the two radiation images or the DXA scanning image, and a pixel value of a bone region in the bone part image obtained by extracting the bone part, which is derived by energy subtraction processing of performing weighting subtraction on the two radiation images or the DXA scanning image.

7. The estimation device according to claim 1, wherein the two-dimensional bone density is derived from the bone part image.

8. The estimation device according to claim 7, wherein the two-dimensional bone density is derived based on a body thickness distribution of the subject estimated based on the radiation image or the DXA scanning image, an imaging condition in a case of acquiring the radiation image or the DXA scanning image, and a pixel value of a bone region in the bone part image.

9. An estimation method comprising:

using a trained neural network that derives an estimation result relating to a three-dimensional bone density of a bone part from a simple radiation image acquired by simply imaging a subject including the bone part, or a DXA scanning image acquired by imaging the subject by a DXA method to derive the estimation result relating to the three-dimensional bone density of the bone part, wherein the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image of the subject or a bone part image representing the bone part of the subject, the two-dimensional bone density of the bone part included in the radiation image, the DXA scanning image, or the bone part image, and the three-dimensional bone density of the bone part of the subject.

10. A non-transitory computer-readable storage medium that stores an estimation program causing a computer to execute a procedure comprising:

using a trained neural network that derives an estimation result relating to a three-dimensional bone density of a bone part from a simple radiation image acquired by simply imaging a subject including the bone part, or a DXA scanning image acquired by imaging the subject by a DXA method to derive the estimation result relating to the three-dimensional bone density of the bone part, wherein the trained neural network learns using, as teacher data, (i) two radiation images acquired by imaging the subject including the bone part with radiation having different energy distributions or the DXA scanning image, and a two-dimensional bone density of the bone part included in the two radiation images or the DXA scanning image, or (ii) the radiation image or the DXA scanning image of the subject or a bone part image representing the bone part of the subject, the two-dimensional bone density of the bone part included in the radiation image, the DXA scanning image, or the bone part image, and the three-dimensional bone density of the bone part of the subject.

* * * * *